United States Patent
Da Silva Rodrigues et al.

(10) Patent No.: US 11,857,804 B2
(45) Date of Patent: Jan. 2, 2024

(54) DETERMINING A MEDICAL IMAGING SCHEDULE

(71) Applicant: KONINKLIJKE PHILIPS N.V., Eindhoven (NL)

(72) Inventors: Pedro Jorge Da Silva Rodrigues, Veldhoven (NL); Vanda Lúcia de Carvalho Vitorino De Almeida, Veldhoven (NL); Reinhold Wimberger Friedl, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 743 days.

(21) Appl. No.: 16/982,614

(22) PCT Filed: Mar. 13, 2019

(86) PCT No.: PCT/EP2019/056221
§ 371 (c)(1),
(2) Date: Sep. 21, 2020

(87) PCT Pub. No.: WO2019/179835
PCT Pub. Date: Sep. 26, 2019

(65) Prior Publication Data
US 2021/0023394 A1    Jan. 28, 2021

(30) Foreign Application Priority Data

Mar. 20, 2018  (EP) .................................... 18162887

(51) Int. Cl.
*A61N 5/10*     (2006.01)
*G16H 20/40*    (2018.01)
*G16H 30/20*    (2018.01)

(52) U.S. Cl.
CPC ........... *A61N 5/103* (2013.01); *A61N 5/1069* (2013.01); *G16H 20/40* (2018.01); *G16H 30/20* (2018.01); *A61N 2005/1052* (2013.01)

(58) Field of Classification Search
CPC ........ G16H 20/40; G16H 30/20; G16H 40/67; G16H 50/50; A61N 5/103; A61N 5/1069;
(Continued)

(56) References Cited

U.S. PATENT DOCUMENTS

2003/0210002 A1    11/2003   Jackson
2007/0041497 A1*    2/2007   Schnarr ................. A61N 5/103
                                                        378/65

(Continued)

OTHER PUBLICATIONS

International Search Report and Written Opinion of PCT/EP2019/056221, dated May 22, 2019.

(Continued)

*Primary Examiner* — Irakli Kiknadze

(57) ABSTRACT

A method (100) is disclosed for determining a medical imaging schedule for a subject receiving treatment at a target site. The method comprises obtaining (102) first blood panel information from a first blood sample acquired from the subject prior to the treatment commencing; obtaining (104) initial imaging data acquired in respect of the target site prior to the treatment commencing; obtaining (106) information regarding the treatment being received; and determining (108), based on at least the first blood panel information, the initial imaging data and the treatment information, a time at which to capture first imaging data in respect of the target site in order to assess a response to the treatment. A system and a computer program product are also disclosed.

15 Claims, 4 Drawing Sheets

(58) Field of Classification Search
CPC .......... A61N 5/1048; A61N 2005/1052; A61N 5/1031; A61N 5/1037; A61N 5/1083; A61N 5/1068; A61N 5/1049; A61N 5/1067; A61N 2005/1059; A61N 5/1077; A61N 5/1039; A61N 2005/1061; A61N 5/1071; A61N 2005/1072; A61N 5/1078; A61N 5/1038; A61N 5/1045; A61N 2005/1054; A61N 5/1075; A61N 5/1065; A61N 2005/1076; A61N 5/1042; A61N 5/107; A61N 5/10; A61B 5/7292; A61B 5/7207; A61B 5/0816; A61B 5/055; A61B 5/103; A61B 5/0044; A61B 5/0022; A61B 6/4014; A61B 6/487; A61B 5/318; A61B 6/5235; A61B 6/03; A61B 6/5294; A61B 6/503; A61B 6/032; G06T 7/13; G06T 7/60; G06T 7/0012; G06T 2207/10116
USPC ...................................................... 378/62, 65
See application file for complete search history.

(56) References Cited

U.S. PATENT DOCUMENTS

| | | | |
|---|---|---|---|
| 2007/0041499 A1 | 2/2007 | Lu | |
| 2007/0189591 A1* | 8/2007 | Lu .......................... | A61N 5/103 382/128 |
| 2011/0112351 A1* | 5/2011 | Fordyce, II ............ | A61N 5/103 600/1 |
| 2012/0220640 A1 | 8/2012 | Ashdown | |
| 2013/0124163 A1 | 5/2013 | Beckman | |
| 2015/0177250 A1 | 6/2015 | Leontovich | |
| 2017/0216624 A1 | 3/2017 | Kondziolka | |
| 2017/0140109 A1 | 5/2017 | Kheifetz | |
| 2017/0235892 A1 | 8/2017 | Sevenster | |
| 2017/0360356 A1 | 12/2017 | Ashdown | |
| 2018/0286508 A1 | 10/2018 | Leontovich | |

OTHER PUBLICATIONS

Juergens, Rosalyn A. et al "Imaging Biomarkers in Immunotherapy, Supplementary Issue: Biomarkers and their Essential Role in the Development of Personalised Therapies (A)", Biomarkers in Cancer, vol. 8 (S2). 2016, pp. 1-13.

Michael Hettich et al "High-Resolution PET imaging with therapeutic antibody-based PD-1/PD-L1 checkpoint tracers", THERANOSTICS, vol. 6, Issue 10, 2016, pp. 1629-1640.

Olafsen, Tove et al "Sensitivity of 89Zr-labeled anti-CD8 minibody for PET imaging of infiltrating CD8+ T cells" Cancer Research, 2016.

Florence Colliez et al "Assessing Tumor Oxygenation for Predicting Outcome in Radiation Oncology: A Review of Studies Correlating Tumor Hypoxic Status and Outcome in the Preclinical and Clinical Settings", Frontiers in Oncology, vol. 7, Article 10, 2017.

Mark W. Dewhirst et al "Oxygen-Enhanced MRI Is a Major Advance in Tumor Hypoxia Imaging". Cancer Research, vol. 76, No. 4, 2016, pp. 769-772.

Raphael Serre et al, "Mathematical Modeling of Cancer Immunotherapy and Its Synergy with Radiotherapy" Cancer Research, vol. 76, No. 17. Sep. 1, 2016, pp. 4932-4940.

Priti S. Hegde et al. "The Where, the When, and the How of Immune Monitoring for Cancer Immunotherapies in the Era of Checkpoint Inhibition", Clinical Cancer Research, vol. 22, No. 8, Apr. 15, 2016, pp. 1865-1874.

* cited by examiner

DETERMINING A MEDICAL IMAGING SCHEDULE

CROSS-REFERENCE TO PRIOR APPLICATIONS

This application is the U.S. National Phase application under 35 U.S.C. § 371 of International Application No. PCT/EP2019/056221, filed on Mar. 13, 2019, which claims the benefit of European Patent Application No. 18162887.6, filed on Mar. 20, 2018. These applications are hereby incorporated by reference herein.

FIELD OF THE INVENTION

The invention relates to decision support in the field of medical imaging. More particularly, the invention relates to determining a medical imaging schedule.

BACKGROUND OF THE INVENTION

When a subject undergoes a medical treatment, it is often useful to carry out an assessment of the subject after the treatment has been administered to determine the extent to which the subject is responding to the treatment. The assessment may, for example, involve acquiring medical imaging data, for example by capturing a medical image using known medical imaging modalities, such as computed tomography (CT), positron emission tomography (PET), single photon emission computed tomography (SPECT), magnetic resonance (MR), ultrasound (US), or a hybrid imaging modality involving a combination of imaging techniques.

One such treatment in which post-treatment imaging is used is cancer immunotherapy. Cancer immunotherapy involves using a subject's immune system to fight cancerous cells in the subject. One type of cancer immunotherapy is immune checkpoint therapy. Immune checkpoints act as regulators of a subject's immune system. These regulatory pathways prevent the subject's immune system from attacking cells which should not be attacked. In immune checkpoint therapies, inhibitory checkpoint molecules are used to block certain receptors, such as CTLA4 (cytotoxic T-lymphocyte-associated protein 4), PD-1 (programmed cell death protein 1) and PD-L1 (programmed death-ligand 1), which inhibit the subject's immune system from fighting the cancer (i.e. killing cancer cells).

Currently, following a treatment being administered to a subject, a post-treatment assessment may be made by capturing medical imaging data at a defined time after the treatment has commenced. For example, a CT scan may be performed on the subject three months after commencement of the treatment. In some cases, further assessments (e.g. further medical scans) may be made at periodic times, such as every three months or every six months. However, by scanning a subject at standard, arbitrary intervals, important developments in the progression of the treatment and/or the development of the cancer may be missed. For example, an individual scan image taken at a particular time may show a positive response as a result of the treatment. However, the response may be temporary (e.g. the cancer may worsen shortly after the scan is performed) and, therefore, the scan may be misleading to a medical professional reviewing the scan results.

It would be useful to be able to scan a subject more regular intervals after treatment has commenced, for example daily. However, the cost, the required manpower, the medical resources (e.g. scanning instruments) and the logistics (e.g. arranging for the subject to be located conveniently for daily scanning) involved in such regular imaging is prohibitive, so such regular imaging is not feasible.

Therefore, it would be desirable to be able to determine more appropriate times at which to perform a scan of a subject after treatment has commenced. Performing a scan at a time appropriate to the particular subject, rather than at an arbitrary time, may assist a treatment provider in assessing whether the treatment is effective, so that alternative or supplementary action may be taken if needed.

SUMMARY OF THE INVENTION

There is a need to be able to determine an appropriate time or times to perform imaging of a subject in order to assess the response to a treatment being provided to that subject. The inventors have discovered that an appropriate (e.g. optimal) time for imaging the subject can be determined based on a number of parameters, including parameters specific to the subject, and information relating to the treatment being administered.

According to a first aspect, the invention provides a method for determining a medical imaging schedule for a subject receiving treatment at a target site. The method comprises obtaining first blood panel information from a first blood sample acquired from the subject prior to the treatment commencing; obtaining initial imaging data acquired in respect of the target site prior to the treatment commencing; obtaining information regarding the treatment being received; and determining, based on at least the first blood panel information, the initial imaging data and the treatment information, a time at which to capture first imaging data in respect of the target site in order to assess a response to the treatment.

In some embodiments, the method may further comprise obtaining clinical information relating to the target site from a biopsy of the target site acquired prior to the treatment commencing. Determining the time at which to capture the first imaging data may be further based on the clinical information.

Determining the time at which to capture the first imaging data may, in some embodiments, comprise inputting the first blood panel information, the initial imaging data, the treatment information and the clinical information into a model describing an expected response to the treatment.

The determining may be based at least in part on the nature of an imaging modality to be used to capture the first imaging data. The imaging modality to be used to capture the first imaging data may be selected from a group comprising: computed tomography (CT), positron emission tomography (PET), single photon emission computed tomography (SPECT), magnetic resonance (MR), ultrasound (US), and a hybrid imaging modality.

The method may further comprise obtaining second blood panel information from a second blood sample acquired from the subject after the treatment has commenced. In some embodiments, the method may further comprise updating the determined time at which to capture first imaging data based on the obtained second blood panel information.

The method, in some embodiments, may further comprise obtaining second blood panel information from a second blood sample acquired from the subject after the treatment has commenced. The method may further comprise updating the model based on the second blood panel information.

The blood panel information may comprise information relating to one or more blood biomarkers.

In some embodiments, the method may comprise determining, based at least on the obtained blood panel information, the obtained initial imaging data and the obtained treatment information, a time at which to capture second imaging data in respect of the target site in order to assess the response to the treatment.

According to some embodiments, the treatment may comprise an immunotherapy treatment. The target site may comprise a tumor.

In some embodiments, the method may comprise obtaining immunohistochemical information relating to the target site. The method may comprise comparing the immunohistochemical information with the initial imaging data.

The time at which to capture first imaging data may correspond approximately to the time at which an initial response to the treatment may be observable.

According to a second aspect, the invention provides a system for determining a medical imaging schedule for a subject receiving treatment at a target site. The system comprises a memory comprising instruction data representing a set of instructions. The system further comprises a processor configured to communicate with the memory and to execute the set of instructions. The set of instructions, when executed by the processor, may cause the processor to obtain first blood panel information acquired from a first blood sample taken from the subject prior to the treatment commencing. The set of instructions, when executed by the processor, may cause the processor to obtain initial imaging data acquired in respect of the target site prior to the treatment commencing. The set of instructions, when executed by the processor, may cause the processor to obtain information regarding the treatment being received. The set of instructions, when executed by the processor, may cause the processor to determine, based on at least the first blood panel information, the initial imaging data and the treatment information, a time at which to capture first imaging data in respect of the target site in order to assess a response to the treatment.

In some embodiments, the set of instructions, when executed by the processor, may cause the processor to obtain second blood panel information from a second blood sample acquired from the subject after the treatment has commenced. The set of instructions, when executed by the processor, may cause the processor to update the determined time at which to capture first imaging data based on the obtained second blood panel information.

In some embodiments, the set of instructions, when executed by the processor, may cause the processor to obtain clinical information relating to the target site from a biopsy of the target site acquired prior to the treatment commencing. The set of instructions, when executed by the processor, may cause the processor to input the first blood panel information, the initial imaging data and the clinical information into a model describing an expected response to the treatment.

In some embodiments, the set of instructions, when executed by the processor, may cause the processor to determine, based on at least the obtained blood panel information and the obtained initial imaging data, a schedule for capturing further imaging data in respect of the target site in order to assess the response to the treatment.

According to a third aspect, the invention provides a computer program product comprising a non-transitory computer readable medium, the computer readable medium having computer readable code embodied therein, the computer readable code being configured such that, on execution by a suitable computer or processor, the computer or processor is caused to perform one or more of the methods disclosed herein. In the context of this non-transitory computer readable medium and for the execution of the computer readable code, when the computer or processor performs a step of obtaining information or data, this means the respective information of data is retrieved from a data storage.

These and other aspects of the invention will be apparent from and elucidated with reference to the embodiments described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF EMBODIMENTS

In a general sense, embodiments disclosed herein relate to a mechanism by which a medical imaging schedule may be determined which is specific to a particular subject undergoing a particular type of treatment. An appropriate time at which to perform a first imaging scan after treatment has commenced may be determined. In some embodiments described herein, a schedule of further imaging scans may also be determined. Thus, the disclosure can be considered to relate to an imaging decision support (IDS) system. Such an IDS system may be used to determine (e.g. predict) an optimal time for image-based assessment of a response to treatment (e.g. immunotherapy). The IDS system may include a dynamic account of the immune system behavior in response to different types of therapy, and the immune system behavior is used to determine the best moment in time at which to capture an image.

Some embodiments are described herein in the context of immunotherapy treatments. However, it will be appreciated that the methods and systems disclosed are applicable to other types of treatment.

Figure 1:
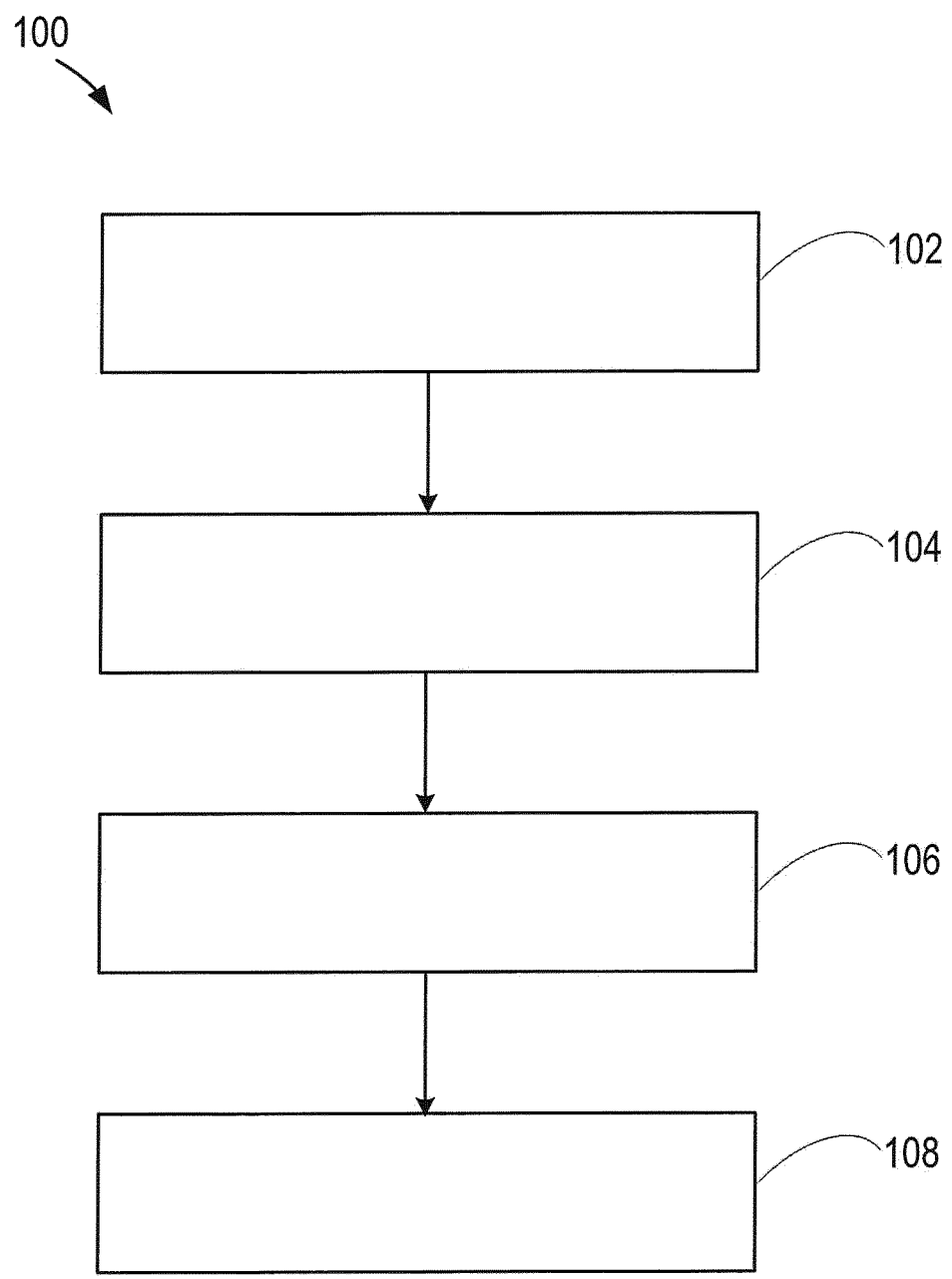
FIG. 1 is a flowchart of an example of a method for determining a medical imaging schedule according to various embodiments.

Referring to the drawings, FIG. 1 is a flowchart of an example of a method 100 for determining a medical imaging schedule for a subject receiving treatment at a target site. The term "subject" is intended to refer to a person or animal in respect of whom the method may be performed. For example, the subject may be a person suffering from cancer in one or more organs of their body. Thus, the "target site" is intended to refer to a site within the subject's body, such as a tumor or lesion, which is present as a result of the disease (e.g. the cancer). While the treatment may be applied to areas on or in the subject other than, or in addition to, the target site, it will be understood that the treatment is intended to ultimately improve the medical condition of the subject at the target site. For example, a treatment may be intended to kill cancer cells at a target site, thereby preventing the growth of a tumor at the target site.

The method 100 comprises, at step 102, obtaining first blood panel information from a first blood sample acquired from the subject prior to the treatment commencing. A blood panel is a blood test or group of tests performed on the blood of a subject from which various components of the blood may be measured. A blood panel involves the analysis of a blood sample which may, for example, be extracted from a vein of the subject. Thus, the blood panel information may be acquired from blood extracted from the subject at a location other than the target site. In this way, blood panel information can be considered to provide systemic information about the subject. In some examples, the blood panel information may include blood biomarkers (e.g. a measurable indicator of the presence of a particular state, such as a disease state or physiological state, of the subject).

By acquiring the blood panel information from a blood sample obtained from the subject prior to the treatment commencing, it is possible to determine a baseline reference with which subsequent blood panels (i.e. blood panel information obtained from blood samples acquired after treatment has commenced) may be compared. The type of information extracted from the blood panel may vary on a case-by-case basis (e.g. based on the subject and the treatment being administered). In some examples, however, blood panel information may include data relating to relevant cells and proteins in the blood. For example, a leukocytes panel may provide data including measurements of myeloid-derived suppressor cells (MDSC), monocytes, macrophages, neutrophils eosinophils, basophils, lymphocytes, and/or platelets. An inflammatory panel may provide data relating to inflammatory proteins such as CRP, IL2, IL6, IL8, TNFalpha and/or a vascular endothelial growth factor (VEGF). A coagulation panel may provide data relating to hematocrit, PR, aPTT, Fibrinonogen, fibrin and/or thrombin. A blood panel may provide data including measurements of regulatory T-cells, measurements of eosinophils, data relating to an epidermal growth factor (EGF), measurements of interleukins, measurements of cytokines and data relating to electrolytes, such as urate, calcium, sodium, potassium and/or magnesium). In some examples, other information may be extracted from blood samples. In some examples, circulating tumor cells (CTC), circulating cell-free tumor DNA (ct-DNA), or circulating lysosomes may be measured and characterized.

The blood panel information obtained at step 102 may, in some embodiments, be obtained from a series of blood samples obtained from the subject at different times prior to treatment commencing.

The blood panel information may be stored in a database having been acquired from the blood sample previously. The step 102 of obtaining the blood panel information may involve retrieving the information or data from a database.

At step 104, the method 100 comprises obtaining initial imaging data acquired in respect of the target site prior to the treatment commencing. As will be appreciated by those skilled in the relevant field, various medical imaging technologies may be used to image the target site within a subject. For example, imaging modalities such as computed tomography (CT), positron emission tomography (PET), single photon emission computed tomography (SPECT), magnetic resonance (MR), ultrasound (US), or a hybrid imaging modality involving a combination of imaging techniques are amongst those techniques suitable for acquiring image data from the target site.

In the field of immunotherapy, various other imaging techniques may be implemented. For example, in-vivo imaging of PD-L1 expression (i.e. imaging the visible development of the programmed death-ligand 1 receptor) may involve a combination of positron emission tomography and computed tomography (PET/CT) or a combination of single positron emission computed tomography and computed tomography (SPECT/CT), using a therapeutic anti-PD-L1 antibody that is labelled with a radioisotope (i.e. a radioactive tracer). In other examples, a radiopharmaceutical known as fludeoxyglucose (FDG) may be used as a radioactive tracer in PET/CT imaging. Other radioactive tracers may alternatively be used, such as 18F-fluorothymidine, 18F-fluorocholine or other markers for tumor proliferation or metabolism. Other antibodies may be used in conjunction with a radioisotope, such as anti-CD8, anti-CD4, or anti-PD-1.

In another example, an immunotherapy treatment may require the in-vivo imaging of an anti-CD8 antibody (CD8 stands for "Cluster of Differentiation 8", a transmembrane glycoprotein that serves as a co-receptor for the T-cell receptor). The anti-CD8 antibody may be coupled with a relatively short-lived radioactive tracer suitable for PET imaging. Another example may require imaging of an anti-PD 1 (i.e. programmed cell death) protein. An anti-PD 1 agent may be coupled with a medium-lived radioactive tracer suitable for PET imaging.

Each radioactive tracer may have a different active life, depending on the half-life of the isotope used in the radioactive tracer. Thus, each radioactive tracer may be visible through imaging at a different duration after it has been injected into the subject.

In some embodiments, metabolic states, hypoxia states and/or vascularization states may be derived from imaging data (e.g. from PET/CT imaging and/or from MR imaging) obtained prior to the treatment commencing. Information on PD-L1 tumor expression characterization and a prior CD8 tumor lymphocytes infiltration may be derived from anti-PD-L1 and anti-CD8 PET imaging.

Different imaging modalities have different imaging sensitivities and, as such, some modalities may not be able to image subtle or small changes in the subject's tissue as a result of the treatment. Therefore, different imaging modalities may be appropriate for capturing images at different times after treatment has commenced.

The initial imaging data obtained at step 104 may be acquired using any suitable imaging modality before the treatment has begun. Such initial imaging data may provide information regarding the target site (e.g. the location and size of a tumor or lesion), and may provide a baseline reference with which to compare imaging data acquired after the treatment has commenced. In some examples, the initial imaging data may be acquired, then stored in a database. The step 104 of obtaining the initial imaging data may involve retrieving the data from a database.

The method 100 comprises, at step 106, obtaining information regarding the treatment being received. The particular disease from which the subject is suffering may determine the nature of the treatment to be administered. Similarly, the treatment to be administered may determine the duration after the treatment has commenced when imaging the target site is appropriate (e.g. an approximate time when a radioactive tracer will be most visible).

At step 108, the method 100 comprises determining, based on at least the first blood panel information, the initial imaging data and the treatment information, a time at which to capture first imaging data in respect of the target site in order to assess a response to the treatment. The "first imaging data" to be captured is the first imaging data following the treatment commencing. In other words, while the "initial imaging data" refers to imaging data acquired prior to the treatment being administered, the "first imaging data" refers to imaging data to be acquired after the initial administration of the treatment.

As noted above, different imaging modalities are suitable for imaging the subject at different times, for example depending on the response kinetics. Therefore, the determination of the image capturing time, made at step 108, may take into account the imaging modality to be used to capture the first imaging data. Thus, in some embodiments, the determination made at step 108 may be based at least in part on the nature of an imaging modality to be used to capture the first imaging data. This may, for example, be incorporated into the initial imaging data used in the determining step 108, particularly if the first post-treatment imaging uses the same imaging modality as the initial (pre-treatment) imaging. Any suitable imaging modality may be used. In some embodiments, however, the imaging modality to be used to capture the first imaging data may be selected from a group comprising: computed tomography (CT), positron emission tomography (PET), single photon emission computed tomography (SPECT), magnetic resonance (MR), ultrasound (US), and a hybrid imaging modality.

The determination made at step 108 is based at least on the information and data obtained in steps 102, 104 and 106. In some embodiments, as discussed in greater detail below, other information and data may also be used in the determining step 108.

The first blood panel information may be used in the determining step 108 as an indication of the presence of various elements at the target site. For example, the detection of a particular component of blood from the blood panel may be extrapolated to determine an amount of that component at the target site. As noted above, the initial imaging data may be used in the determining step 108 as an indication of the location and/or size of a lesion or tumor, for example. The initial imaging data may also provide an indication of the extent to which cancer cells have spread beyond a particular location (e.g. the target site) prior to the treatment being administered. As noted above, the information regarding the treatment being received provides treatment-specific details, such as the optimum time to perform a first imaging scan for the particular treatment being administered.

The determining 108 may provide an output in the form of a time or duration after the initial administration of the treatment (e.g. n minutes, n hours, n days, n weeks, and so on) at which first imaging data should be captured or acquired to view the effects of the treatment in an optimal manner. In some examples, an output may be provided in the form of a range of times within which the first imaging data should be captured or acquired.

In its simplest sense, the step of determining 108 may be achieved using databases and/or look up tables. For example, a particular combination of information acquired from the first blood panel information, initial imaging data and treatment information may correspond to a particular duration after commencing treatment, or a particular range of times following the commencement of treatment, at which the first imaging data should be captured. In other examples, as discussed in greater detail below, the information and data obtained in steps 102, 104 and 106 may be provided as inputs to a model for determining the time at which to capture the first imaging data.

Figure 2:
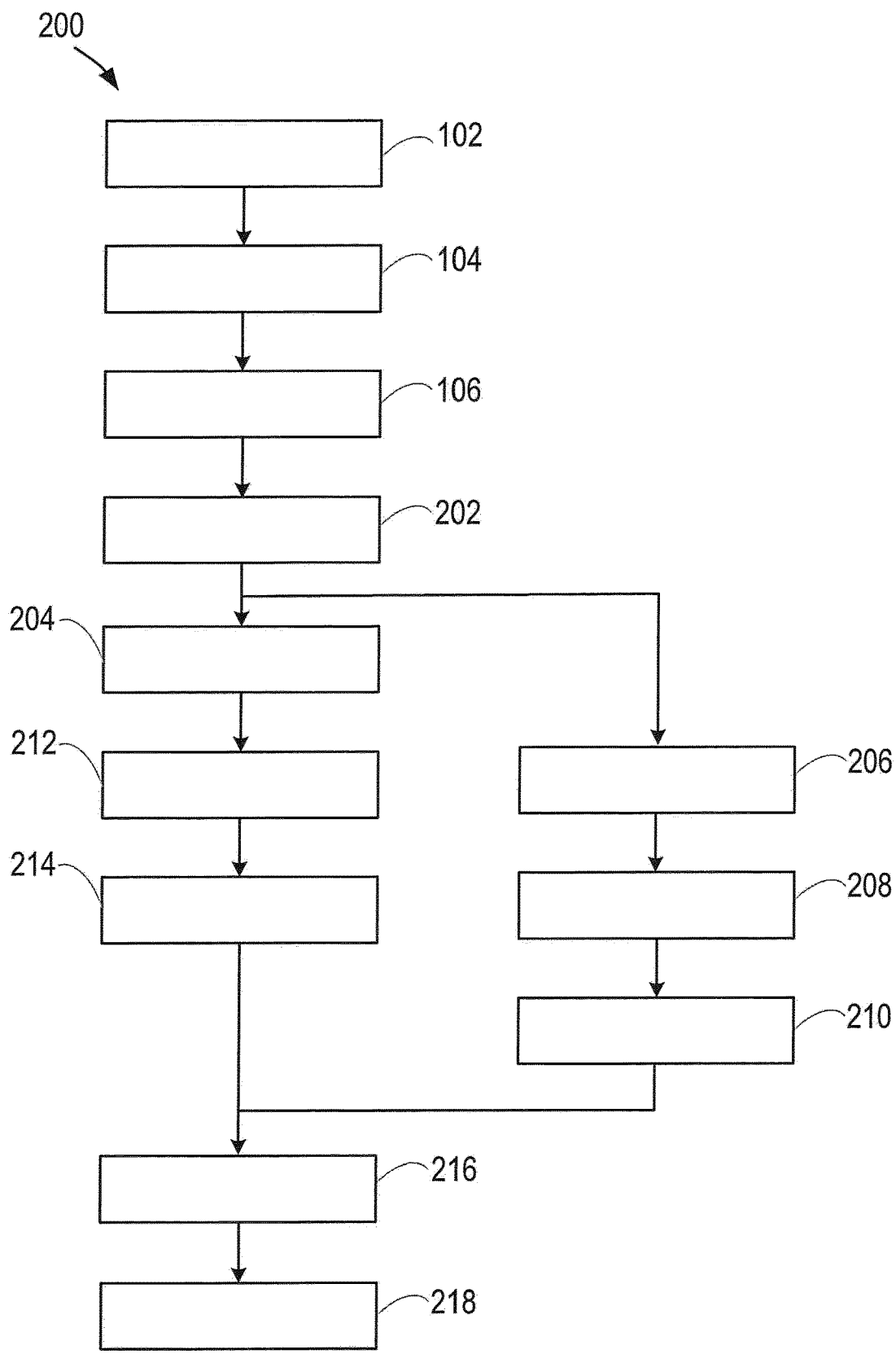
FIG. 2 is a flowchart of a further example of a method for determining a medical imaging schedule according to various embodiments.

FIG. 2 is a flowchart of a further example of a method 200 for determining a medical imaging schedule for a subject receiving treatment at a target site. The method 200 may include steps of the method 100 discussed above. For example, the method 200 comprises the steps of obtaining first blood panel information (step 102), obtaining initial imaging data (step 104) and obtaining information regarding the treatment being received (step 106). In some embodiments, the method 200 may further comprise, at step 202, obtaining clinical information relating to the target site from a biopsy of the target site acquired prior to the treatment commencing. In embodiments in which clinical information is obtained, the method 200 may comprise, at step 204, determining, based on at least the first blood panel information, the initial imaging data, the treatment information and the clinical information, a time at which to capture first imaging data in respect of the target site in order to assess a response to the treatment. In other words, determining the time at which to capture the first imaging data (step 108) is further based on the clinical information.

A biopsy of the target site may provide useful information regarding the target site (e.g. the tumor or lesion) which may be used to determine a time at which to capture the first imaging data. For example, tumor characteristics may be derived from a biopsy performed on a tumor at the target site. In some examples, immunohistochemical (IHC) data may be acquired from a biopsy using techniques that will be familiar to those skilled in the relevant field. Information on PD-L1 tumor expression characterization and a prior CD8 tumor lymphocytes infiltration may be obtained from biopsy IHC information.

As noted above, the step of determining the time at which to capture the first imaging data may be performed using a model, with the information and data obtained at steps 102, 104 and 106 provided as inputs into the model. In embodiments in which clinical information is obtained (e.g. at step 202), the clinical information may also be provided as an input into a model. Thus, determining the time at which to capture the first imaging data comprises inputting the first blood panel information, the initial imaging data, the treatment information and the clinical information into a model describing an expected response to the treatment. In other words, the method 200 may, in some embodiments, comprise, at step 206, determining the time at which to capture first imaging data by inputting the first blood panel information, the initial imaging data, the treatment information and the clinical information into a model describing an expected response to the treatment. The model may be referred to as a time-dependent immune response (TDIR) model. The model (e.g. a TDIR model) may be based on initial target site characteristics (e.g. tumor characteristics), an initial environment of the target site (e.g. an initial tumor environment) and initial diagnostic blood characterization (e.g. blood panel information from a blood sample acquired from the subject prior to the treatment commencing). When run or executed with the inputs mentioned above, the model provides as its output the time (e.g. an optimum time) at which to capture the first imaging data (i.e. the first imaging data after treatment has commenced).

As noted above, response kinetics (i.e. physical changes resulting from the treatment) may be taken into account along with the sensitivity of the imaging modality to be used in order to determine a suitable (e.g. an optimal) time at which to capture the first imaging data.

In examples where the treatment site is, or includes, a tumor, the model may include or incorporate a tumor growth model which predicts the growth of the tumor over time. The tumor growth model may be dynamic; that is to say, the tumor growth model may vary or be adapted over time as the rate of growth of the tumor changes, for example as a result of the treatment or of changes in the subject.

The method 200 may further comprise, at step 208, obtaining second blood panel information from a second blood sample acquired from the subject after the treatment has commenced. For example, after commencing the treatment, one or more further blood samples may be acquired from the subject (e.g. by performing one or more blood tests) and blood panel information may be obtained from each of the further blood samples. In some examples, further blood samples (e.g. the second and subsequent blood samples) may be acquired at regular intervals following the treatment commencing. In other examples, the further blood samples may be acquired at some other time-dependent frequency which may, for example, be defined by a set of rules. The rules defining when further blood samples should be acquired from the subject following the start of the treatment may be defined based, for example, on the type of treatment being administered. For example, the rules may specify that further blood samples are to be acquired after a duration t following the start of the treatment as this is when the beginning of a response is to be expected. The rules may be based on the treatment scheme being administered, patient characteristics, and one or more other factors. In some examples, the rules may be defined prior to treatment. However, the rules may be modified as treatment progresses, for example based on feedback from blood panel information or images/scans acquired after treatment has commenced.

At step 210, the method 200 may further comprise updating the determined time calculated using the model, based on the second blood panel information. Thus, parameters provided to the model used at step 206 to determine the time at which to capture the first imaging data may be adjusted or updated based on the second blood panel information acquired from second blood sample. The second blood panel information acquired from the second blood sample may, for example, indicate that the subject has responded unexpectedly (e.g. in a negative way) to the treatment and, therefore, it may be desirable to adjust the model so that the first imaging data is to be captured sooner. In this way, any negative effects may be identified quickly, so that any necessary remedial action or changes in the treatment regime may be taken.

In embodiments in which a model is not used to determine the timing of the first imaging data acquisition, the method 200 may proceed from step 204 to step 212, which comprises obtaining second blood panel information from a second blood sample acquired from the subject after the treatment has commenced (i.e. the same as step 206). Following step 212, however, the method 200 may comprise, at step 214, updating the determined time at which to capture first imaging data based on the obtained second blood panel information. Thus, even though the timing may not be determined using a model, the determined time may be updated based on the second blood panel information obtained from the second blood sample. It is noted that, in some embodiments, the determined time may be updated (step 214) without the first-determined imaging schedule (i.e. the imaging time determined at step 108) having been implemented. In other words, a second blood sample acquired before the determined imaging schedule is implemented may reveal information that prompts the determination to be made again to determine a new time at which to capture the first imaging data.

As noted briefly above, blood panel information may comprise information relating to one or more of blood biomarkers, cytokines, leukocyte panel information, CTCs, and ct-DNA.

In an example in which a model is used to determine timings for acquiring images after the treatment has begun, such a model may be used to determine an appropriate time (e.g. an optimal time) to acquire PD1/CD8 immuno-PET images in order to determine whether CD8 T-cells are able to infiltrate a tumor at a target site upon PD-L1 inhibition. In addition to determining an appropriate time for the first post-treatment image acquisition, an imaging schedule may be determined, for example using the model. Thus, the method may determine or suggest times at which to acquire further images in order to monitor the effectiveness of the treatment and/or the progression of the disease. For example, a model may provide a suggestion to acquire an image to monitor PD1 expression, using a suitable radioactive tracer. Similarly, the model may provide an output suggesting that an anti-PD-L1 PET image should be acquired to confirm that a therapeutic anti-PD-L1 agent has adequately been able to block PD-L1 over-expression at the target site (i.e. on the tumor).

In addition to determining a time at which to capture first imaging data (e.g. a time at which to perform a first imaging scan) following the beginning of the administration of the treatment, the method according to some embodiments may determine a time or times at which to capture additional imaging data. For example, a schedule of imaging events may be determined. Referring again to FIG. 2, the method 200 may comprise, at step 216, determining, based at least on the obtained blood panel information, the obtained initial imaging data and the obtained treatment information, a time at which to capture second imaging data in respect of the target site in order to assess the response to the treatment. Thus, in some embodiments, the method may also determine times at which to capture third, fourth, fifth (and so on) imaging data. An imaging schedule determined at step 216 may be revised or updated based, for example, on blood panel information obtained subsequent to the first blood panel information. For example, if the second blood panel information reveals that an unexpected treatment response has occurred, then the schedule (e.g. the determined time at which to capture second imaging data) may be revised by the method 200. In some embodiments, an imaging schedule which includes appropriate (e.g. optimum) times for acquiring third and/or fourth (or subsequent) imaging data may be revised or updated based on information acquired in the second imaging data. In general, each newly-acquired imaging data may affect the imaging schedule going forward. For example, a set of acquired imaging data may show a particular response which would warrant bringing forward the next scheduled scan.

As noted above, while embodiments are described in the context of medical treatments in general, according to some embodiments, the treatment may comprise an immunotherapy treatment, and the target site may comprise a tumor.

According to some embodiments, as noted above, immunohistochemical (IHC) information may be used to derive details of tumor expression and/or tumor infiltration by particular entities associated with the treatment. Thus, the method 200 may, in some embodiments, further comprise obtaining immunohistochemical information relating to the target site. The target site may, for example, comprise a tumor. However, for some target sites (e.g. tumors or lesions), IHC information may not be available, or it may not be possible to obtain such IHC information from a biopsy of the target site. In such cases, equivalent or similar information may be obtainable from IHC information from an alternative site and from imaging data acquired in relation to the alternative site and the target site.

In some embodiments, the determined time at which to capture first imaging data may correspond approximately to the time at which an initial response to the treatment may be observable. In other words, the time determined at step 108 may correspond to the earliest time at which any evidence of a treatment response might be expected in view of the sensitivity of the imaging modality in question. Capturing an image before this time is unlikely to provide much, if any, benefit as no response to the treatment is likely to be visible in an image. However, capturing an image, or multiple images around the time, or soon after the time, of an initial response to the treatment being visible may be particularly useful as any temporary peak in treatment response (e.g. corresponding to a temporary reduction in growth of a tumor) followed by a reduction in treatment response may be detectable if appropriate imaging is performed around this time.

In some embodiments, any of the obtained information or data (e.g. the information and data obtained at steps 102, 104, 106, 202, 208 and 212) and any of the determined times (e.g. the times determined at steps 108 and 216) may be delivered for presentation to a user (e.g. a medical professional) or presented to the user. For example, data may be presented on a display associated with workstation, a computer terminal, or some other computing device or mobile device.

Figure 3:
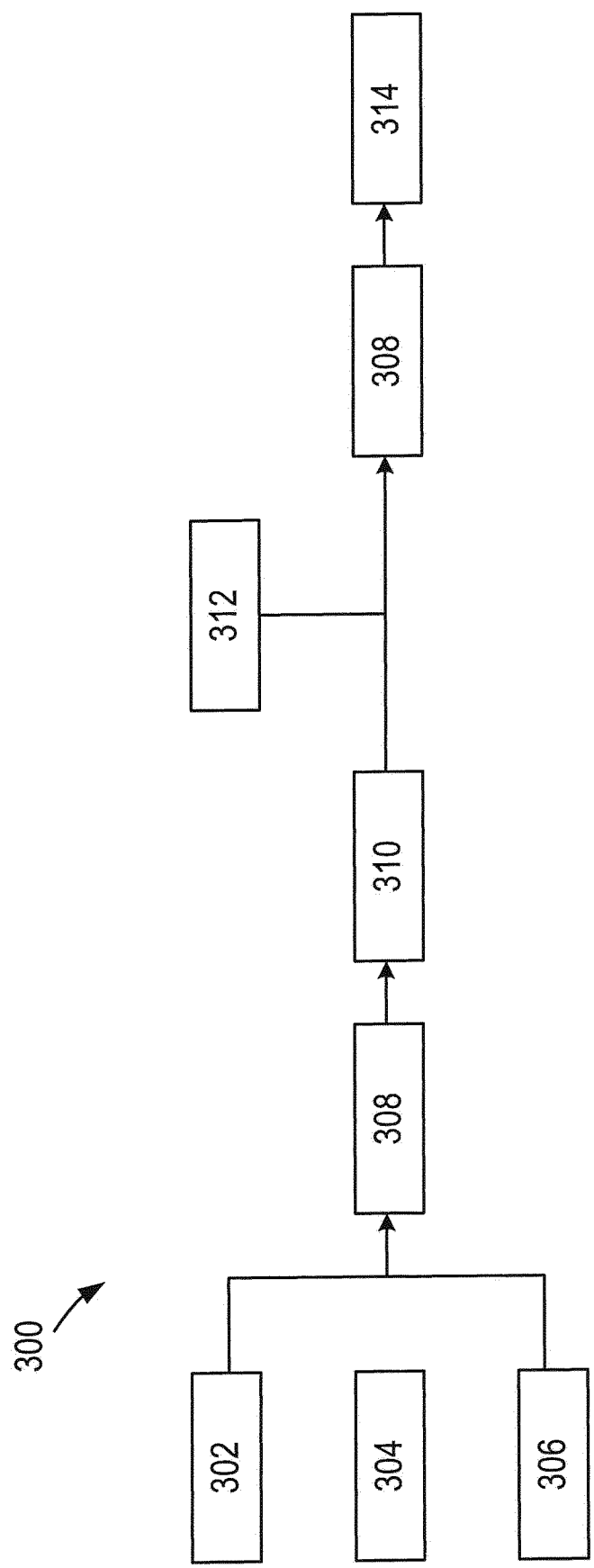
FIG. 3 is a block diagram showing information pathways in an example of a method for determining a medical imaging schedule according to various embodiments.

An example of a method according to one embodiment will now be discussed with reference to FIG. 3. The method discussed with reference to FIG. 3 may be performed with respect to a subject undergoing treatment (e.g. immunotherapy treatment) at a target site (e.g. a cancerous tumor). FIG. 3 is a block diagram showing the information pathways between various elements. In this example, blood panel information 302, clinical information 304 from a biopsy and initial imaging data 306 are provided as inputs to a model. The blood panel information 302 may, for example, comprise the first blood panel information obtained at step 102 of the method 100, which may include blood indicators or biomarkers. The clinical information 304 may comprise information from a biopsy of the target site acquired prior to treatment commencing, as obtained at step 202 of the method 200. The initial imaging data 306 may comprise the data obtained at step 104 of the method 100. The model 308 may comprise a time-dependent immune response (TDIR) model as discussed above. The model 308 may further be provided with information regarding the treatment being provided to the subject.

Based on the various inputs, the model 308 outputs an imaging schedule 310. The image schedule 310 may include one or more times at which to capture imaging data in respect of the target site in order to assess the response to the treatment. Following the determination of an initial imaging, additional blood panel information 312 may be acquired, for example through additional blood samples acquired from the subject. The additional blood panel information 312 may be provided as an input to the model 308. Based on the additional blood panel information 312, an updated imaging schedule 314 is generated. One or more further blood samples may be acquired, as needed, and the model 308 may be used to generate further updated imaging schedules based on blood panel information obtained from the further blood samples.

The additional blood samples 312 may comprise samples obtained at step 212 of the method 200. Similarly, the updated imaging schedule 314 may comprise a schedule updated at step 214 of the method 200. In some embodiments, the additional blood panel information 312 may indicate that the model 308 should be run again with new, revised input parameters. For example, a significant difference between the (initial) blood panel information 302 and the additional blood panel information 312 may be evident. In such a case, parameters input to the model 308 may be adjusted or revised so that a more appropriate output from the model may be achieved.

Blood panel information obtained from the first blood sample and from subsequent blood samples (e.g. the additional blood panel information 312) may be used to provide systemic information relating to the subject. For example, the blood panel information may provide details of the overall immune system of the subject. By acquiring additional blood samples from the subject after treatment has begun, blood panel information from those additional blood samples may be used to determine whether the overall immune system is responding to the treatment. An example of an indicator of the overall system response is the balance of CD8 and CD4 cells. For example, if, from additional blood panel information 312, it is apparent that the CD8/CD4 balance has become unfavorable (e.g. by an increase in the number of CD4 cells in relation to the number of CD8 cells), then the model 308 may output a revised imaging schedule which recommends that an imaging scan should take place earlier than initially scheduled.

In embodiments in which a model is used to determine the time at which to capture first imaging data, the model may include various components, each of which focuses on a different aspect relevant to the time at which the imaging data is to be captured. As discussed above, various inputs may be provided to the model. A first input may involve tumor spatial characterization which may, for example, be obtained or extracted from the initial imaging data. The spatial characterization of the tumor may, for example, be obtained from CT scans, FDG PET scans, or MR scans. A second input may involve tumor cellular characterization which may, for example, be obtained or extracted from the clinical information from a biopsy of the target site. The cellular characterization of the tumor may, for example, be obtained from IHC measurements or immune-PET scans. A third input may involve blood panels which may, for example, be obtained from blood samples acquired from the subject prior to the treatment commencing. As discussed above, blood panel information may include data relating to leukocytes, inflammatory proteins, coagulation information and/or electrolytes. A fourth input may involve information relating to the type of treatment or therapy to be administered to a subject.

Within the model, a first component may consider tumor proliferation; a second component may consider tumor killing by effector cells; a third component may consider recruitment of effector cells; and a fourth component may consider expansion of effector cells. One or more of the model components may be combined in order to generate an output of the model.

A first output of the model may comprise a measurement of the volume of the tumor, or an estimated or predicted tumor volume, based on the inputs provided. The second output the model may comprise the time at which the first imaging data (after treatment has commenced) should be acquired or captured. The time at which to capture the first imaging data may also depend on the imaging modality to be used, and this may be referred to as an image response function. The model may take the imaging modality into consideration when generating its outputs. The model may, for example, consider noise, blurring and/or spatial resolution in the imaging modality to be used.

Figure 4:
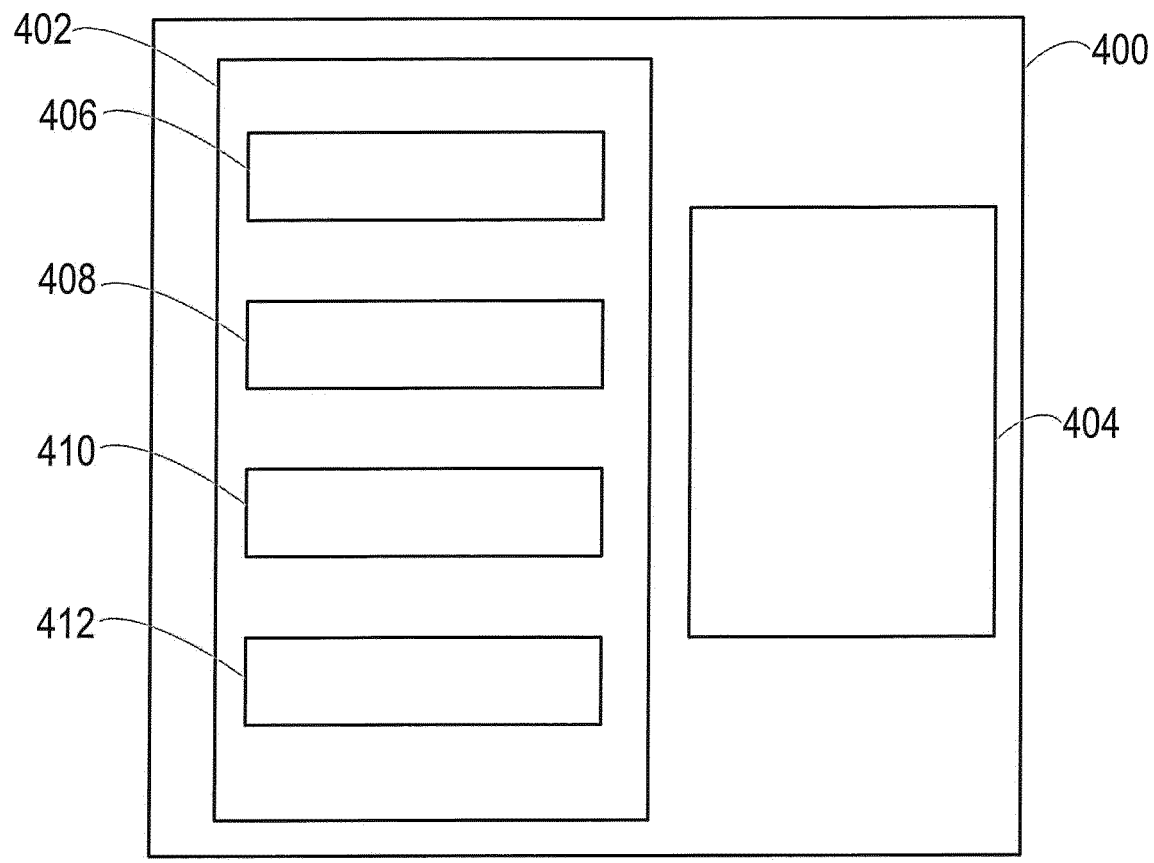
FIG. 4 is a simplified schematic of an example of a system for determining a medical imaging schedule according to various embodiments.

According to a further aspect, embodiments relate to a system for performing the methods disclosed herein. FIG. 4 is a simplified schematic of a system 400 for determining a medical imaging schedule for a subject receiving treatment at a target site. The system 400 comprises a memory 402 comprising instruction data representing a set of instructions. The system 400 also comprises a processor 404 configured to communicate with the memory and to execute the set of instructions. The set of instructions, when executed by the processor 404, cause the processor to obtain first blood panel information acquired from a first blood sample taken from the subject prior to the treatment commencing. The memory may, therefore, comprise first blood panel information obtaining instructions 406. The set of instructions, when executed by the processor 404, further cause the processor to obtain initial imaging data acquired in respect of the target site prior to the treatment commencing. The memory may, therefore, comprise initial imaging data obtaining instructions 408. The set of instructions, when executed by the processor 404, further cause the processor to obtain information regarding the treatment being received. The memory may, therefore, comprise treatment information obtaining instructions 410. The set of instructions, when executed by the processor 404, cause the processor to determine, based on at least the first blood panel information, the initial imaging data and the treatment information, a time at which to capture first imaging data in respect of the target site in order to assess a response to the treatment. The memory may, therefore, comprise time determination instructions 412.

According to some embodiments, the set of instructions, when executed by the processor 404, may cause the processor to obtain second blood panel information from a second blood sample acquired from the subject after the treatment has commenced. The set of instructions, when executed by the processor 404, may further cause the processor to update the determined time at which to capture first imaging data based on the obtained second blood panel information According to some embodiments, the set of instructions, when executed by the processor 404, may cause the processor to obtain clinical information relating to the target site from a biopsy of the target site acquired prior to the treatment commencing. The set of instructions, when executed by the processor 404, may further cause the processor to input the first blood panel information, the initial imaging data and the clinical information into a model describing an expected response to the treatment According to some embodiments, the set of instructions, when executed by the processor 404, may cause the processor to determine, based on at least the obtained blood panel information and the obtained initial imaging data, a schedule for capturing further imaging data in respect of the target site in order to assess the response to the treatment.

The system 400 may, for example, comprise a workstation, a computer terminal or some other computing device or mobile device having suitable processing functionality.

Figure 5:
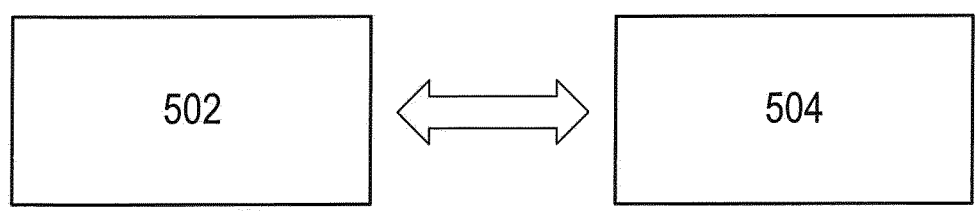
FIG. 5 is a simplified schematic of an example of a computer-readable medium and a processor.

According to a further aspect, embodiments relate to a computer program product. FIG. 5 is simplified schematic of a computer-readable medium and a processor. According to some embodiments, a computer program product comprises a non-transitory computer readable medium 502, the computer readable medium having computer readable code embodied therein, the computer readable code being configured such that, on execution by a suitable computer or processor 504, the computer or processor is caused to perform the methods disclosed herein. In the context of this non-transitory computer readable medium and for the execution of the computer readable code, when the computer or processor is caused to performs a step of obtaining information or data, this means the respective information of data is retrieved from a data storage.

The processor 404, 504 can comprise one or more processors, processing units, multi-core processors or modules that are configured or programmed to control the system 400 in the manner described herein. In particular implementations, the processor 404, 504 can comprise a plurality of software and/or hardware modules that are each configured to perform, or are for performing, individual or multiple steps of the method described herein.

The term "module", as used herein is intended to include a hardware component, such as a processor or a component of a processor configured to perform a particular function, or a software component, such as a set of instruction data that has a particular function when executed by a processor.

It will be appreciated that the embodiments of the invention also apply to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to embodiments of the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for determining a medical imaging schedule for a subject receiving treatment at a target site, the method comprising:
    obtaining first blood panel information from a first blood sample acquired from the subject prior to the treatment commencing;
    obtaining initial imaging data acquired in respect of the target site prior to the treatment commencing;
    obtaining information regarding the treatment being received; and
    determining, based on at least the first blood panel information, the initial imaging data and the treatment information, a time at which to capture first imaging data in respect of the target site in order to assess a response to the treatment.

2. A method according to claim 1, further comprising:
    obtaining clinical information relating to the target site from a biopsy of the target site acquired prior to the treatment commencing;
    wherein determining the time at which to capture the first imaging data is further based on the clinical information.

3. A method according to claim 2, wherein determining the time at which to capture the first imaging data comprises inputting the first blood panel information, the initial imaging data, the treatment information and the clinical information into a model describing an expected response to the treatment.

4. A method according to claim 1, wherein the determining is based at least in part on the nature of an imaging modality to be used to capture the first imaging data.

5. A method according to claim 4, wherein the imaging modality to be used to capture the first imaging data is selected from a group comprising: computed tomography (CT), positron emission tomography (PET), single photon emission computed tomography (SPECT), magnetic resonance (MR), ultrasound (US), and a hybrid imaging modality.

6. A method according to claim 1, further comprising:
    obtaining second blood panel information from a second blood sample acquired from the subject after the treatment has commenced; and
    updating the determined time at which to capture first imaging data based on the obtained second blood panel information.

7. A method according to claim 1, further comprising:
    determining, based at least on the obtained blood panel information, the obtained initial imaging data and the obtained treatment information, a time at which to capture second imaging data in respect of the target site in order to assess the response to the treatment.

8. A method according to claim 7, wherein the treatment comprises an immunotherapy treatment, and the target site comprises a tumor.

9. A method according to claim 8, further comprising:
    obtaining immunohistochemical information relating to the target site; and
    comparing the immunohistochemical information with the initial imaging data.

10. A method according to claim 8, wherein the time at which to capture first imaging data corresponds approximately to the time at which an initial response to the treatment may be observable.

11. A computer program product comprising a non-transitory computer readable medium, the computer readable medium having computer readable code embodied therein, the computer readable code being configured such that, on execution by a suitable computer or processor, the computer or processor is caused to perform the method of claim 1.

12. A system for determining a medical imaging schedule for a subject receiving treatment at a target site, the system comprising:
    a memory comprising instruction data representing a set of instructions; and
    a processor configured to communicate with the memory and to execute the set of instructions, wherein the set of instructions, when executed by the processor, cause the processor to:
    obtain first blood panel information acquired from a first blood sample taken from the subject prior to the treatment commencing;
    obtain initial imaging data acquired in respect of the target site prior to the treatment commencing;
    obtain information regarding the treatment being received; and
    determine, based on at least the first blood panel information, the initial imaging data and the treatment information, a time at which to capture first imaging data in respect of the target site in order to assess a response to the treatment.

13. A system according to claim 12, wherein the set of instructions, when executed by the processor, cause the processor to:
    obtain second blood panel information from a second blood sample acquired from the subject after the treatment has commenced; and
    update the determined time at which to capture first imaging data based on the obtained second blood panel information.

14. A system according to claim 12, wherein the set of instructions, when executed by the processor, cause the processor to:
    obtain clinical information relating to the target site from a biopsy of the target site acquired prior to the treatment commencing;
    input the first blood panel information, the initial imaging data and the clinical information into a model describing an expected response to the treatment.

15. A system according to claim 12, wherein the set of instructions, when executed by the processor, cause the processor to:
    determine, based on at least the obtained blood panel information and the obtained initial imaging data, a schedule for capturing further imaging data in respect of the target site in order to assess the response to the treatment.

\* \* \* \* \*